(12) United States Patent
Marcoux (10) Patent No.: US 7,858,512 B2
(45) Date of Patent: Dec. 28, 2010

(54) SEMICONDUCTOR WITH BOTTOM-SIDE WRAP-AROUND FLANGE CONTACT

(75) Inventor: Phil P. Marcoux, Mountain View, CA (US)

(73) Assignee: Wafer-Level Packaging Portfolio LLC, Cupertino, CA (US)

( * ) Notice: Subject to any disclaimer, the term of this patent is extended or adjusted under 35 U.S.C. 154(b) by 204 days.

(21) Appl. No.: 12/147,375

(22) Filed: Jun. 26, 2008

(65) Prior Publication Data

US 2009/0321930 A1 Dec. 31, 2009

(51) Int. Cl.
*H01L 21/44* (2006.01)

(52) U.S. Cl. .................. 438/612; 438/110; 438/112; 438/458; 438/459; 438/460; 257/741; 257/735; 257/774

(58) Field of Classification Search ................. 438/612, 438/110, 112, 113, 458, 459, 460, 462, 613, 438/617
See application file for complete search history.

(56) References Cited

U.S. PATENT DOCUMENTS

| | | | |
|---|---|---|---|
| 4,673,967 A | 6/1987 | Hingorany | |
| 5,910,687 A | 6/1999 | Chen et al. | |
| 6,051,489 A | 4/2000 | Young et al. | |
| 6,221,751 B1 * | 4/2001 | Chen et al. | 438/612 |
| 6,355,981 B1 * | 3/2002 | Richards et al. | 257/735 |
| 6,441,487 B2 | 8/2002 | Elenius et al. | |
| 6,521,970 B1 | 2/2003 | Takiar et al. | |
| 6,589,819 B2 | 7/2003 | Smith et al. | |
| 6,638,870 B2 | 10/2003 | Brintzinger et al. | |
| 6,946,734 B2 | 9/2005 | Marcoux et al. | |
| 7,205,659 B2 | 4/2007 | Beroz et al. | |
| 7,622,810 B2 * | 11/2009 | Takao | 257/774 |

FOREIGN PATENT DOCUMENTS

| | | |
|---|---|---|
| JP | 9129675 A | 5/1997 |
| JP | 2000003976 A | 1/2000 |
| KR | 1020000070442 A | 11/2000 |
| WO | 9852224 A1 | 11/1998 |

OTHER PUBLICATIONS

Verdant Electronics, Inc. "Robust, Simplified and Solder-Free Assembly Processing of Electronics Products", Sunnyvale, California, 24 Pages.

(Continued)

*Primary Examiner*—N Drew Richards
*Assistant Examiner*—Mamadou Diallo
(74) *Attorney, Agent, or Firm*—Edward P. Heller, III (57) ABSTRACT

A packaging technique for electronic devices includes wafer fabrication of flexible contacts on the bottom surface of the substrate underneath the active circuit. Inherently reliable contacts suitable for a variety of devices can be formed via a simple fabrication process with good wafer packing density. For one embodiment, a trench is formed from the back of the substrate, exposing an upper conductive layer on the top surface. A standoff is formed on the bottom surface of the substrate. A lower conductive layer is formed that runs from and electrically connects with the exposed portion of the upper conductive layer onto the substrate standoff. The standoff is removed, releasing the formed conductors, resulting in a flexible contact.

8 Claims, 6 Drawing Sheets

OTHER PUBLICATIONS

W.E. Jahsman et al., Comparison of Predicted and Measured Lead Stiffness of Surface Mounted Packages, Intel Corporation, Electronic Components and Technology Conference, 1990 Proceedings, 40th, vol. 2, pp. 926-932 (May 20-23, 1990).

ATMEL, 64K (8K x 8) Parallel EEPROMs; AT28C64, AT28C64X, Dec. 1999, 12 pages.

Texas Instruments, TM124MBK36F, TM124MBK36U, 1048576 by 36-Bit DRAM Module; TM248NBK36F, TM248NBK36U 2097152 by 36-Bit DRAM Module.

\* cited by examiner

SEMICONDUCTOR WITH BOTTOM-SIDE WRAP-AROUND FLANGE CONTACT

FIELD

Embodiments of the present invention relate generally to electronic component packaging. More particularly, these embodiments relate to a wafer level processing for an electronic component packaging having a bottom-side wrap-around flange contact.

BACKGROUND

Electronic components are packaged in order to interconnect them with other devices. The packaging of the electronic device usually includes contacts for transmitting signals and providing power and ground connections between the internal circuitry of the device and external circuitry. Some examples of prior art contacts include wire bonds protruding from the ends of a discrete diode or resistor, or metal caps located on the ends of a fuse. Sophisticated electronic devices such as microprocessors may require several hundred contacts. Those devices are usually produced in a package having multiple pins for mounting to a printed circuit. The electronic component is typically placed in a package, and each contact area on the electronic component is wire bonded to the corresponding pin on the package. Because each wire bond is individually added to the circuit, large numbers of contacts make wire bonding expensive. Additionally, because of the precision required for wire bonding, wire bonding may result in short circuits and similar problems. Furthermore, wire bonds can degrade chip performance because of the length of the wires.

One prior art method of solving the problems of wire bonds is the flip chip. Solder balls act as attachment material that allows the flip chip to be attached to a substrate or circuit board. The silicon of the flip chip usually has a different coefficient of thermal expansion (CTE) than that of the substrate or circuit board. The CTE for the flip chip can be as low as 3 parts per million (PPM) while the substrate or circuit board (as well as the solder balls) can be in the range of 18-22 PPM. As a result of the CTE mismatch, the chip and substrate or circuit board expand and contract at different rates due to thermal cycling. A lack of compliance in the contact area can cause failures. Attempts to solve the CTE mismatch have included introducing large volumes of solder. This is contrary, however, to the desires of the market for electronic packaging for smaller, cheaper, and faster components. For example, in U.S. Pat. No. 6,441,487, the inventors specify a minimum sized solder ball that is 229 um (0.009") as a means of improving reliability. The market is seeking the ability to use solder balls smaller than 100 um (0.004").

U.S. Pat. No. 4,673,967 presented a plastic leaded chip carrier (PLCC) with J-shaped device leads soldered to respective portions of circuit pads on a printed circuit board to minimize space, dissipate heat, and provide some compliancy to a dual in-line package (DIP) for integrated circuits. This PLCC requires a multitude of manufacturing steps, however, such as wire bonding, which includes the complications discussed above, and results in a relatively large package.

U.S. Pat. No. 6,221,751 presented a circuit package which addressed CTE mismatch by providing lead connections that are not directly on the surface of the die, but instead formed on posts composed of an encapsulant material. This allows for some compliancy and smaller bond pads or junction areas on the die and thus minimizes the stress on the die surface. Nevertheless, greater flexibility and compliancy is still desired.

SUMMARY

A method is described for fabricating a contact for an electronic device. The bottom surface of a substrate is thinned. The substrate has an electronic circuit that includes a electrical connection point on the top surface of the substrate. The thinning exposes a portion of the bottom surface of the electrical connection point. A standoff is formed below the bottom surface of the substrate. A lower conductive layer is formed that runs from the standoff and runs to and electrically couples with the exposed portion of the electrical connection point. At least a portion of the standoff is removed to form the flexible conductor.

An electronic component package is also described that includes a flexible conductor on a bottom side of a substrate. The substrate has an electronic circuit. A gap of air defines the space between a portion of the flexible conductor and a portion of the bottom side of the substrate.

Other features and advantages of embodiments of the present invention will be apparent from the accompanying drawings and from the detailed description that follows.

BRIEF DESCRIPTION OF THE DRAWINGS

Embodiments of the present invention are illustrated by way of example and not limitation in the figures of the accompanying drawings, in which like references indicate similar elements, and in which.

DETAILED DESCRIPTION

A method and apparatus are described for an electronic component package using wafer level processing and flexible contacts on the bottom side of the substrate under an active or passive circuit. For one embodiment, a trench is formed from the back of the substrate, exposing the contacts on the top surface. A standoff is formed below the bottom surface of the substrate. A lower conductive layer is formed that runs from and electrically connects with the exposed portion of the upper conductive layer onto the substrate standoff. The standoff is removed, releasing the formed conductors, resulting in a flexible contact. Once the floating flexible conductor is formed and the device is soldered to a circuit board, the conductor will flex to absorb the size changes resulting from the mismatch of coefficients of thermal expansion. By forming the contacts on the bottom side of the device, the amount of interference caused by operating at very high frequencies and radiated energy from nearby devices is reduced.

Figure 1A:
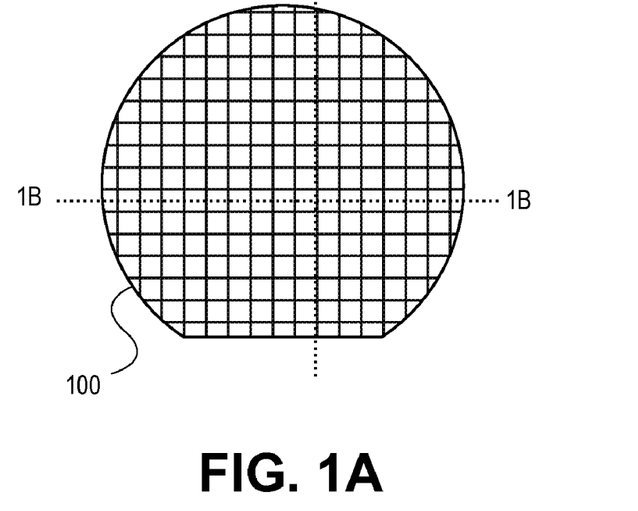
FIG. 1A is a top view of a substrate wafer showing how its top surface is tiled with replications of die, each of which will become an electronic device.
Figure 2:
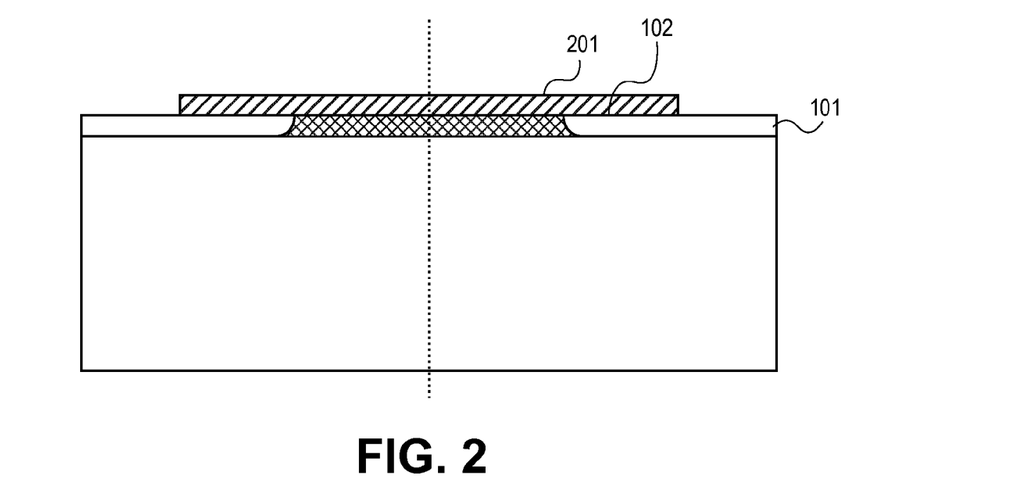
FIG. 2 is a cross-sectional side view of the wafer portion of FIG. 1B after conductive material has been formed on top of the wafer.

FIG. 1A illustrates a top view of substrate wafer 100. FIG. 2 shows a corresponding cross section. The top surface of substrate wafer 100 has been used to fabricate a number of integrated circuits each within a rectangular die that is replicated or tiled across the wafer. Cut line or separation plane 111 is one of the planes along which substrate wafer 100 will be separated or diced into individual electronic devices—finished electronic devices, not merely die requiring a subsequent assembly process.

Any material that is suitable for the fabrication of electronic circuitry and is suitable for shaping via etching, shaving or the like can be used for substrate wafer 100. In some embodiments, substrate wafer 100 is formed of crystalline silicon (Si). Other embodiments use other semiconductors for substrate wafer 100 such as, but not limited to, the following: gallium arsenide (GaAs), silicon germanium (SiGe), silicon carbide (SiC), gallium phosphide (GaP) or the like. For one embodiment, substrate wafer 100 is formed of any III-V semiconductor material. Yet other embodiments use insulative substrates such as, but not limited to, ceramic materials, sapphire, quartz or the like.

Figure 1B:
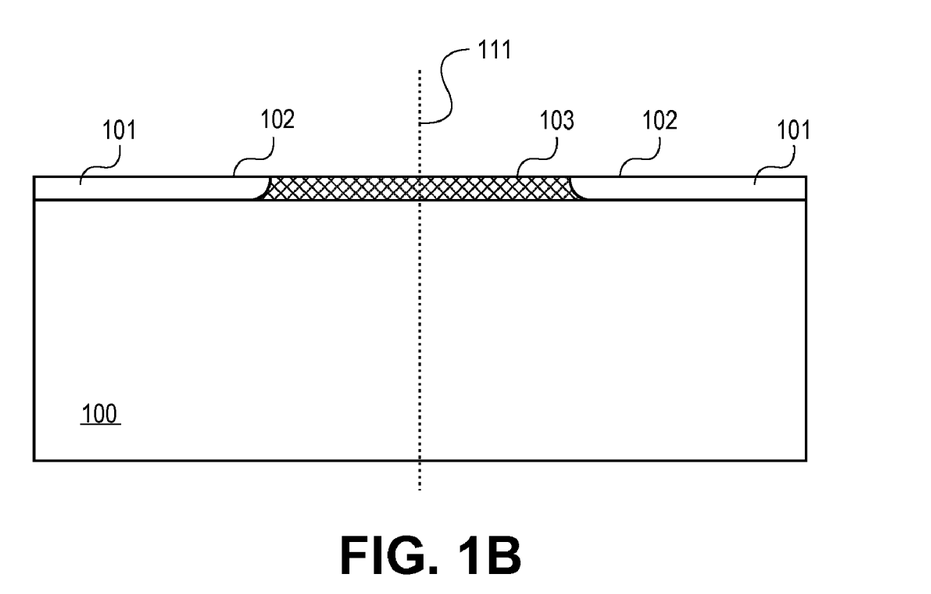
FIG. 1B is a cross-sectional side view of a portion of the wafer showing the electronic circuit or component areas for two adjacent devices, each having a connection point.

A cross-sectional view of substrate wafer 100 is also shown in FIG. 1B, the cross-section being taken along line 1(b). The top surface of substrate wafer 100 has been used to fabricate an integrated circuit within electronic circuit regions 101. Electronic circuit regions 101 include connection points 102. An electrical signal or power supply voltage must be connected between connection points 102 and circuitry external to the finished electronic device in order for it to operate property.

Various techniques for fabricating electronic circuits using substrate wafer 100 are known in the art as well as for attaching fabricated electronic circuits to substrate wafer 100. The description below of the contact fabrication process assumes that the fabrication of the electronic circuit or component or its attachment to substrate wafer 100 has been completed.

Referring to FIGS. 1A and 1B, electrical connection points 101 suggest an integrated circuit that is fabricated using the top surface of substrate wafer 100. Nevertheless, the techniques and embodiments described throughout this disclosure apply to contacts for any electronic circuit or discrete electronic component that can be fabricated using, or attached to, substrate wafer 100. For example, a passive discrete component, such as, but not limited to, a resistor or capacitor, or an active discrete component such as, but not limited to a transistor, power transistor, diode, thrysister, field-effect transistor (FET), or the like could include connection points 102 and could have contacts fabricated according to any of the techniques or embodiments disclosed herein. As a further example without limitation, various integrated circuits or other electronic circuits could be attached to substrate wafers 100 could include connection points 102 and could then have contacts fabricated according to any of the techniques or embodiments disclosed herein.

Generally, an electronic circuit is formed within or attached to square or rectangular shaped electrical connection points 101 that are replicated both horizontally and vertically, covering the top surface of substrate wafer 100. Electrical connection points 101 are gold, silver, nickel, titanium, aluminum, tungsten, copper, platinum, any other conductive material, or combination thereof. Edges of two adjacent electrical connection points 101 are shown in FIG. 1B. Connection points 102 of electrical connection points 101 are typically near those edges, but could be located away from the edge if desired. An insulating layer 103 was deposited and separates electrical connection points 101.

A potential advantage of the present method of fabricating contacts is higher wafer packing density. That is, the area of substrate wafer 100 that must be dedicated to forming contacts might be reduced over that required. This may allow more replications of electrical connection points 101 to fit on a wafer, thus reducing the manufacturing cost for each device.

FIGS. 2-12 show the processing of an electronic component. For one embodiment the processing illustrated below occurs at a wafer level prior to the separation of the wafer into individual dies. Wafer level packaging is advantageous because it permits processing to occur simultaneously for multiple dies, and does not require individual handling of the dies. Furthermore, because the dies are prepared in the same process, uniformity of processing is assured. The figures below illustrate a single die. It is understood, however, that the processing is wafer level and occurs with respect to all dies on the wafer substantially simultaneously.

FIG. 2 illustrates a cross-sectional side view in which the wafer portion of FIGS. 1A and 1B has an upper interconnection conductive layer 201 formed on a region of substrate wafer 100. Interconnection conductive layer 201 extends from connection point 102 within electronic circuit region 101 into the portion of wafer surrounding separation plane 111 (for example, 6 to 10 microns thick and 10 microns wide, or a width going up to whatever is appropriate for the current carried). Any technique of forming interconnection conductive layer 201 can be used, such as, but not limited to, pattern plating, sputter deposition of a metal layer within a low-pressure inert gas followed by photo-lithographically selective etching of that layer, or the like.

Electrical connection points 101 and interconnection conductive layer 201 can be any substance of suitable conductivity—for example, a metal, such as, but not limited to, gold (Au), silver (Ag), copper (Cu), aluminum (Al), nickel (Ni), titanium (Ti), tungsten (W), alloys thereof, or layers thereof. For one embodiment, electrical connection points 101 are aluminum (Al) and interconnection conductive layer 201 is a barrier layer metal composed of layers of titanium (Ti), tungsten (W), nickel (Ni), and gold (Au).

Interconnection conductive layer 201 as well as the other metal conductive layers, interconnect, or contact layers described herein might be advantageously formed of layers of metals, such as, but not limited to, the following: a thin barrier metal layer (as can allow current to flow between certain metals while avoiding the metals directly touching) or a thin seed metal layer (as can facilitate forming a metal layer by plating), followed by a main layer, followed by a gold flash layer (as can resist corrosion).

Figure 3:
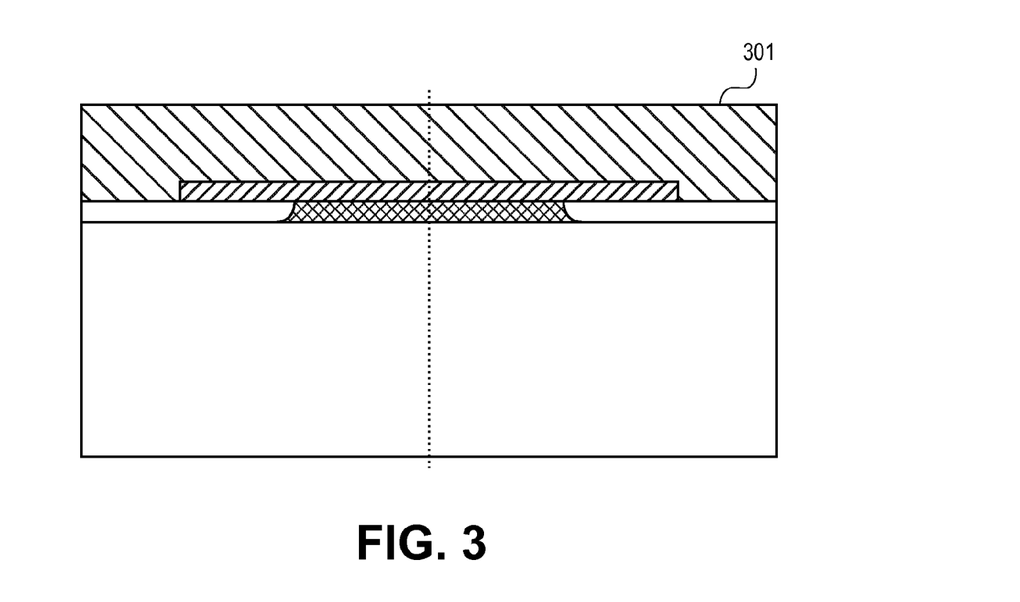
FIG. 3 is a cross-sectional side view of the wafer portion of FIG. 2 after a relatively thick layer of epoxy has been applied to the top of the wafer and the conductive material, which encapsulates them into a strong and rigid unit.

FIG. 3 illustrates a cross-sectional side view of the wafer portion of the FIG. 2 after a relatively thick encapsulation or cover layer 301 (150 microns, for example) of insulation material such as epoxy has been applied to the top of the wafer, which encapsulates substrate wafer 100 and interconnection conductive layer 201 into a strong and rigid unit.

Encapsulant layer 301 can be formed of epoxy, glass, plastic, polymide resins, Teflon, RTM, silicon oxide ($SiO_2$), silicon nitride ($Si_3N_4$), mixtures thereof, layers thereof, or any other material that is non-conducting, relatively rigid and strong, and sufficiently flexible or compliant to allow for thermal expansion both in subsequent wafer processing and in the complete electronic system. Additionally, encapsulant layer holds the wafer flat and rigid when the active substrate is thinned as described herein. For example, Hysol RTM FP4650 epoxy manufactured by Dexter Electronic Materials, a division of Loctite Corporation, located in City of Industry, Calif., might be suitable for encapsulant layer 301. As an alternative to being compliant, encapsulant layer 301 can be formed of a material with thermal expansion characteristics similar to those of substrate wafer 100.

Encapsulant layer 301 can be applied using a variety of techniques. These techniques may attempt to keep encapsulant layer 301 at a uniform thickness, or to eliminate air bubbles within encapsulant layer 301 or between it and substrate wafer 100 and interconnection conductive layer 201. For some embodiments, substrate wafer 100 is spun, possibly in a centrifuge, to form encapsulant layer 301. For alternative embodiments, encapsulant layer 301 comprises a high-temperature insulative epoxy material that is cured in a furnace.

For some embodiments, encapsulant layer 301 can include a top or cap layer (not shown) containing materials, such as, but not limited to, the following: silicon, polysilicon, amorphous silicon, plastic, glass, epoxy, aluminum, diamond, mixtures thereof, layers thereof, or any other material that is relatively rigid and strong. This cap layer can make the finished electronic device more mechanically rugged. It can also serve as a thermal conduit to dissipate heat produced by the operating electronic device. This cap layer need not be an insulator.

Figure 4:
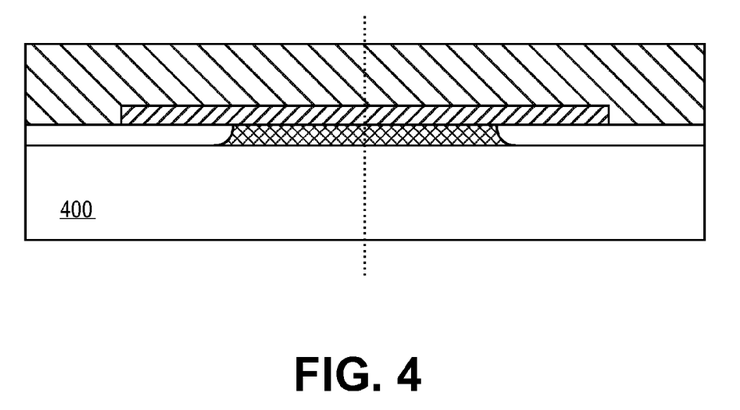
FIG. 4 is a cross-sectional side view of the wafer portion of FIG. 3 after the wafer has been thinned from the bottom.

FIG. 4 illustrates a cross-sectional side view of the wafer portion of the FIG. 3 after substrate wafer 100 is thinned from its bottom surface resulting in thinner substrate wafer 400. Any method of removing substrate material from the back of substrate wafer 100 can be used, such as, but not limited to, back planing, back lapping, sandblasting, grinding, wet chemical etching, dry plasma etching, or the like.

The next step is to selectively remove material from the bottom surface of substrate wafer 400 so as to reduce its substrate thickness along separation plane 111. Any method of selectively removing substrate material from the back of substrate wafer 400 can be used, such as, but not limited to, the following: diamond saw cutting, photo-lithographically selective wet chemical etching, photo-lithographically selective dry plasma, ion etching, or the like.

Figure 5:
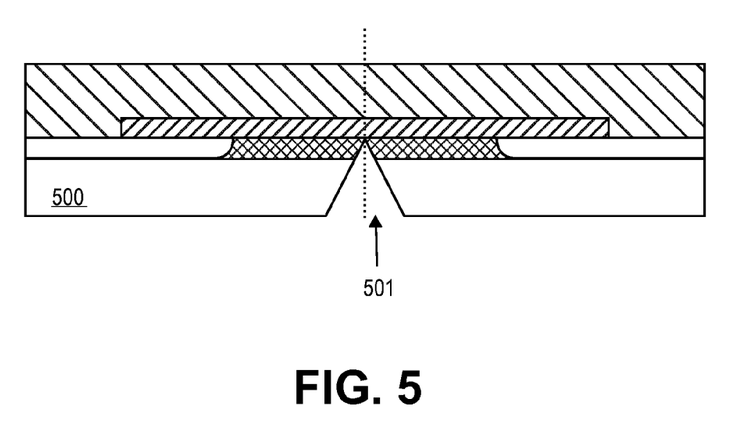
FIG. 5 is a cross-sectional side view of the wafer portion of FIG. 4 after a notch has been cut into the bottom surface of the wafer between adjacent electronic circuits.
Figure 6:
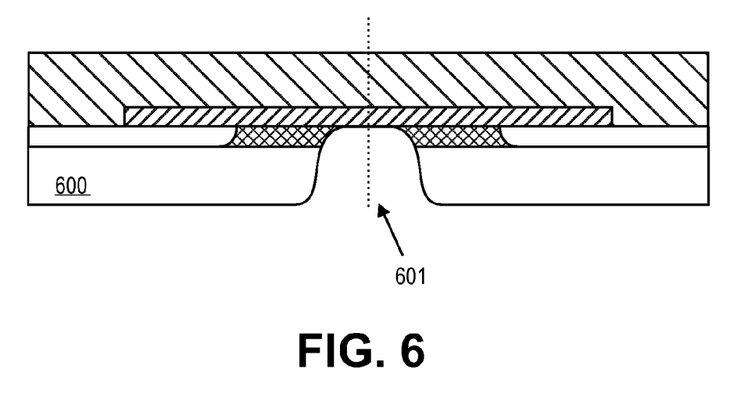
FIG. 6 is a cross-sectional side view of the wafer portion of FIG. 5 after the wafer has been further thinned selectively from the bottom, which exposes the contacts to the substrate.

As illustrated in FIG. 5 and FIG. 6, first a diamond-shaped saw cut 501 can be made through the substrate 500 and then selective etching can be used to broaden the cut 601. For some embodiments, the thinning steps of FIG. 5 and FIG. 6 could be combined into a single step. A sufficient amount of material must be removed that a portion of interconnection conductive layer 201 is exposed on the bottom or the sides of the trench 601.

For one embodiment, the interconnection conductive layer 201 is omitted—e.g., when electrical connection points 101 are made of copper (CU). Without interconnection layer 201, cuts 501 and 601 remove a sufficient amount of material to expose a portion of the bottom of electrical connection points 101 (not shown). This eliminates the need to open the top of electrical connection points 101 for interconnection layer 201, which saves a masking step in the application of the first insulating layer 103. This method also changes the first and final test steps (wafer probe and final test) into one final test point.

Figure 7:
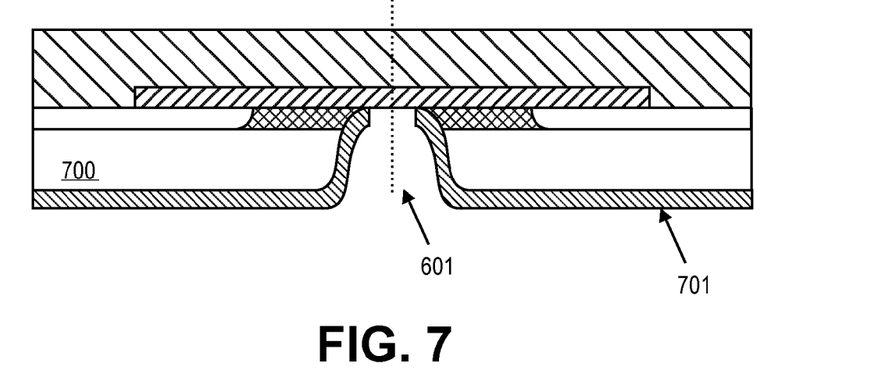
FIG. 7 is a cross-sectional side view of the wafer portion of FIG. 6 after an insulation layer has been applied to the bottom of the wafer and the contacts to the substrate remain exposed.

FIG. 7 illustrates a cross-sectional side view of the wafer portion of the FIG. 6 after an insulating layer 701 has been deposited on the bottom and sides of the substrate. Interconnection conductive layer 201 remains exposed as the result of masking or etching or otherwise removing insulating layer 701 from interconnection conductive layer 201. For one embodiment, this step of depositing insulating layer 701 is omitted—e.g., if the substrate is made of gallium arsenide (GaAs).

Figure 8:
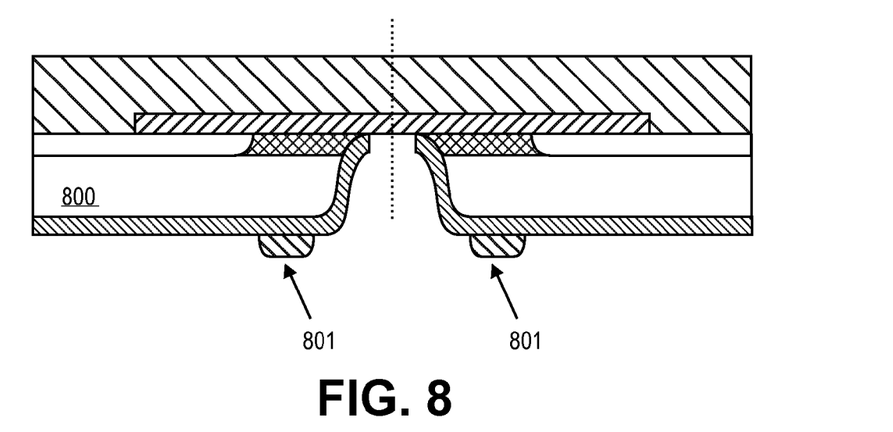
FIG. 8 is a cross-sectional side view of the wafer portion of FIG. 7 after a standoff has been formed on the bottom of the wafer according to a pattern to form the post and shape the conductive layer.

As illustrated in FIG. 8, standoffs 801 are created on the bottom surface of substrate wafer 800 to form posts and shape the conductive layer described below. Standoffs 801 may either be grown, prefabricated and attached, stenciled, or made by other means known in the art. Standoffs 801 are made of polymer plastic, patterned plastic, epoxy, glass, Teflon, silicon dioxide, polysilicon, or any other material which can provide mechanical support for the conductive layer described below. Alternatively, standoffs 801 are made of silicon, gallium arsenide, silicon germanium, silicon carbide, gallium phosphide, ceramic materials, sapphire, quartz, or other substrate materials. For an alternative embodiment (not shown), the standoffs formed will overlap the trench as well as the bottom surface of the substrate wafer 800. For one embodiment, standoffs 801 are between 25 and 200 microns in height.

Figure 9:
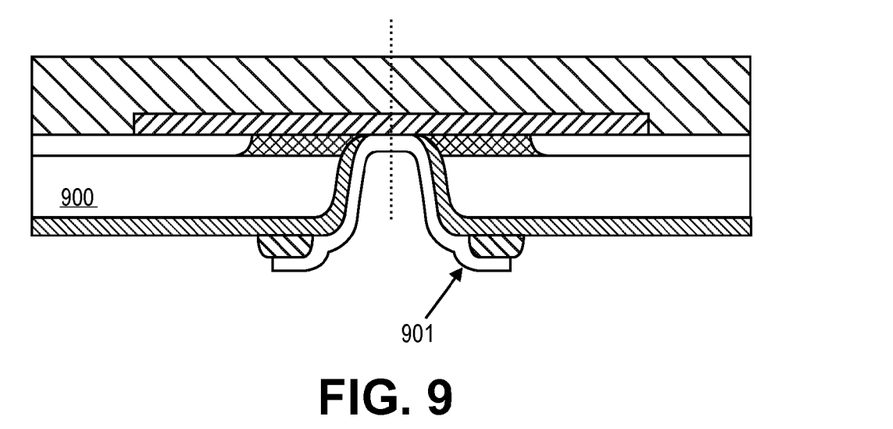
FIG. 9 is a cross-sectional side view of the wafer portion of FIG. 8 after contacts have been formed on the bottom of the wafer according to a pattern.

As illustrated in FIG. 9, lower conductive layer or contact layer 901 is formed on the bottom surface of substrate wafer 900 over the insulating layer 701 and over the standoffs 801 according to a pattern. One portion, relative to each finished device, of contact layer 901 connects with the exposed portion of interconnection conductive layer 201. The other ends of contact layer 901 run onto standoffs 801 thus forming the bottom of each contact being fabricated. Contact layer 901 may end at the inside edge of standoff 801, or it may fully or only partially cover its bottom surface. The bottom surface dimensions of a contact can vary from contact to contact. It is not necessary for any contact to have the same width or the same length as any other contact. The inter-contact pitch can be variable.

For some uses of some types of electronic devices, it potentially is a significant advantage to be able to vary the contact's surface area. In the absence of this ability, if the current carrying capacity of a single contact is exceeded, then multiple contacts must be dedicated to carry the same signal or power-supply voltage level. Also, the ability to vary the contact's surface area might help reduce parasitic circuit elements such as resistance and inductance that can be introduced by a contact. Such a reduction could be a significant advantage in some cases, such as for power switching devices.

Contact layer 901 is formed from a metal or other conductor that facilitates connecting the contacts of the electronic device with the wiring on the surface to which the device is mounted. For embodiments where soldering is used to form connections, contact layer 901 can be made of a conductor such as, but not limited to, the following: nickel (Ni), nichrome-gold, nichrome-nickel, nickel-arsenic-gold, nickel-arsenic, nickel-gold, gold-tin-oxide (ATO), palladium-silicide, titanium (Ti), tungsten (W), titanium-tungsten (Ti—W), indium titanium oxide (ITO), aluminum (Al), copper (Cu), platinum (Pt), alloys thereof or layers thereof. Gold (Au) or silver (Ag) can also be used for contact layer 901.

Any method of forming contact layer 901 according to a pattern can be used, including, but not limited to, pattern plating. Pattern plating is not wasteful of materials and can be faster, and result in a higher quality contact layer 901, than depositing contact layer 901 by evaporation or sputtering.

Various methods of pattern plating are known and can be used to form contact layer 901. One such method is as follows. A first layer (0.2 microns thick, for example) of titanium-tungsten (Ti—W) is deposited on the bottom of substrate wafer 900. A second layer (0.2 microns thick, for example) of gold (Au) is deposited over the first layer. The second layer is then selectively coated by a photo resist layer (6 to 10 microns thick, for example) in the regions where contact layer 901 is not to be formed. Electroplating is then used to form a contact layer 901, which can actually become thicker than the photoresist layer. The photoresist layer is then stripped off and the first and second layers are etched away where they are not protected by contact layer 901.

For one embodiment, prior to depositing the contact layer 901, a barrier metal such as titanium tungsten (Ti/W) is first sputter deposited over the entire circuit and followed by a plating of nickel (Ni) and a flash of gold (Au). Alternatively, copper (Cu) plating is used. The barrier metal provides a barrier layer between metals and enhances adhesion of the contact layer 901. For one embodiment, the upper portion of contact layer 901 (closest to the substrate 900 and interconnection conductive layer 201) and the lower portion of interconnection conductive layer 201 consist of the same conductive material. After the deposition of contact layer 901, the barrier metal layer is etched away from the remaining areas of the electronic component.

Figure 10:
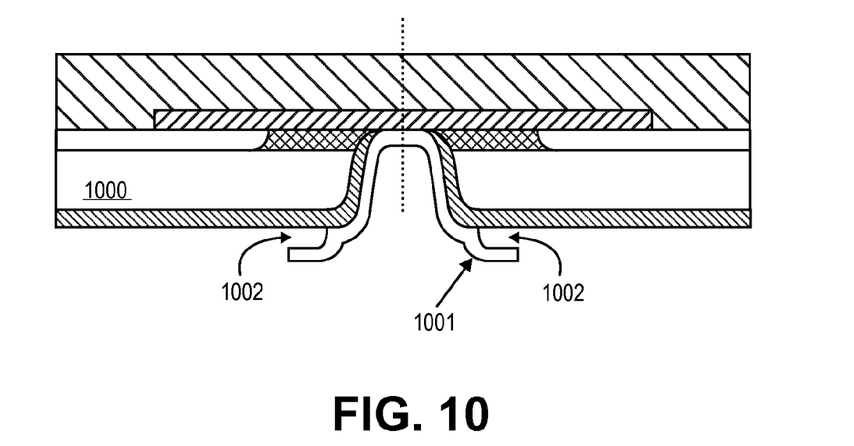
FIG. 10 is a cross-sectional side view of the wafer portion of FIG. 9 after the standoff is removed, releasing the formed conductor, resulting in a flexible contact.

FIG. 10 illustrates the circuit of FIG. 9 with standoffs 801 removed, leaving behind compliant conductive member 1001 and gap 1002. Standoffs 801 can be removed using photo imaging, chemical etching, plasma etching, or other known techniques. For one embodiment, the removal of standoffs 801 includes removing standoff material in the trench 601 (not shown, as described above) creating a larger gap 1002 that extends into the trench 601.

Once the floating flexible conductor 1001 is formed and the device is coupled with a circuit board, the conductor will flex to absorb the size changes, similar to a flange joint, resulting from the mismatch of coefficients of thermal expansion. For one embodiment, the flexible conductor 1001 is patterned to have a suitable surface for coupling with a circuit board via one or more of the following techniques: soldering, ultrasonic bonding, conductive epoxy, or the Occam process. With the Occam process, components are interconnected using copper plating after the components are assembled into their final positions in an encapsulated module. With the Occam process, an assembly containing components is metalized with copper using standard printed circuit build-up processing methods, with circuit patterns created to form the required interconnections between leads of all the components.

As discussed herein, bottom plating layer of flexible conductor 1001 will accept solder—e.g., gold and nickel, while the top of the flexible conductor 1001 will not—e.g., titanium tungsten. If the top of the flexible conductor 1001 accepted solder, solder would be able to flow or reflow all the way around the flexible conductor 1001 due to gap 1002 when being soldered to a circuit board, causing a loss in compliancy.

Figure 11:
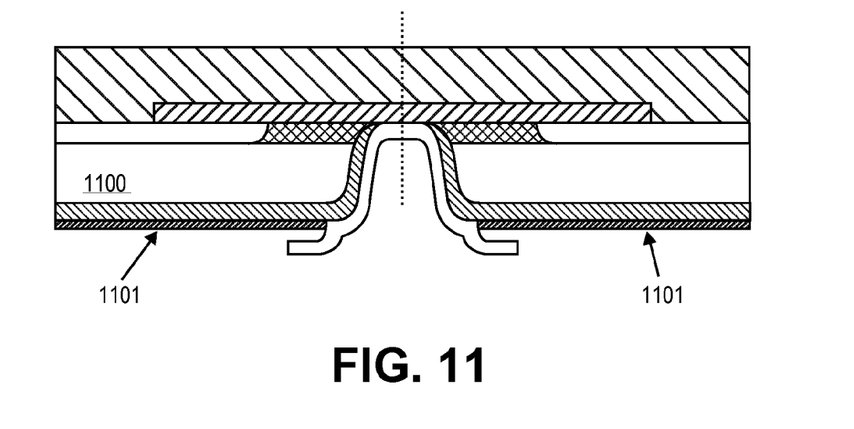
FIG. 11 is a cross-sectional side view of the wafer portion of FIG. 10 after an insulating layer has been deposited on the bottom side of the substrate and a portion of the flexible contact remains exposed.

FIG. 11 illustrates a cross-sectional side view of the wafer portion of the FIG. 10 with coating layer 1101 deposited on the bottom of the of substrate wafer 1100. For one embodiment, coating layer 1101 is a polyimide layer, and is deposited by spinning. Alternatively, the coating layer 1101 is another encapsulant or epoxy. For one embodiment, the coating layer 1101 is not deposited on the top of the flexible conductor 1001. Thus the bottom of flexible conductor 1001 remains electrically conductive. The coating layer 1101 is deposited using a masking process. Alternatively, the coating layer 1101 is deposited uniformly over the entire circuit, and removed from the top of beams 510 using photo imaging techniques. For one embodiment, this step is omitted.

Coating layer 1101 functions as a solder resist. For one embodiment, coating layer 1101 is approximately 25 um thick while the posts stand off the chip approximately 75 to 100 um. Any of coating layer 1101 that remains on the solder surface of flexible conductor 1001 is so thin that the coating layer is easily penetrated and removed during the reflow solder process joining the package to the circuit board. The bulk of the coating layer 1101, however, prevents solder form wicking completely over the beam and rendering the beam rigid.

Figure 12:
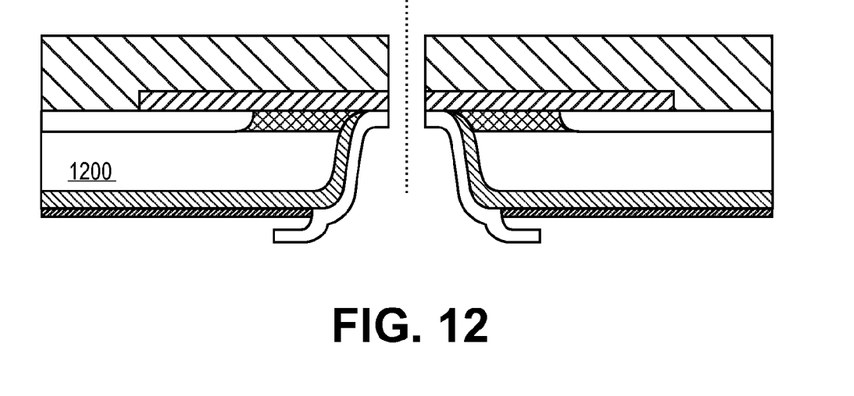
FIG. 12 is a cross-sectional side view of the wafer portion of FIG. 11 after the wafer portion has been diced into two electronic devices, each with an attached, flexible contact.

FIG. 12 illustrates a cross-sectional side view of the wafer portion of FIG. 11 after the wafer portion has been diced into two electronic devices, each with an attached, flexible contact. This separation can be achieved by any method, such as, but not limited to, sawing, etching, or methods known in the art. The separation formed by sawing or etching forms the outside surface of the electronic device.

Figure 13:
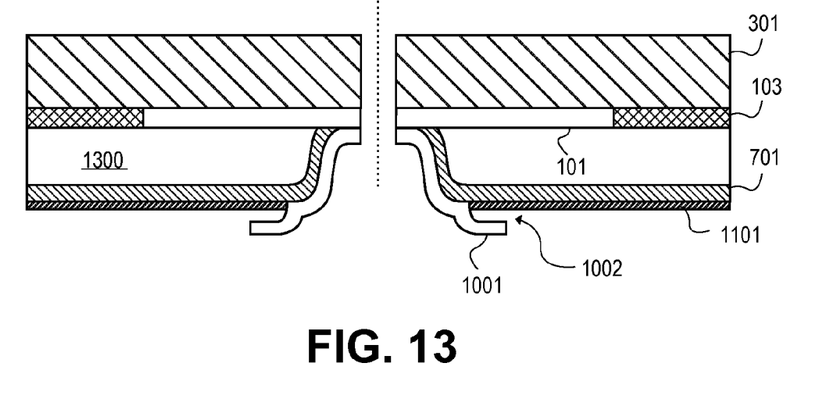
FIG. 13 is a cross-sectional side view according to an embodiment in which the flexible contacts are coupled directly with the electrical connection points.

FIG. 13 is a cross-sectional side view according to an alternative embodiment in which the flexible contacts 1001 are coupled to the electrical connection points 101 directly rather than indirectly by means of the interconnection conductive layer 201. The fabrication of the electronic devices is otherwise similar to the description above in reference to FIGS. 3-12.

For one embodiment, thinning, etching, or cutting 501-601 of the bottom of the device exposes a portion of the bottom surface of one or more electrical connection points 101. An insulating layer 701 is deposited on the bottom and sides of the substrate. Electrical connection points 101 remain exposed as the result of masking or etching or otherwise removing insulating layer 701 from electrical connection points 101. For one embodiment, this step of depositing insulating layer 701 is omitted. Standoffs are created on the bottom surface of the substrate wafer.

The lower conductive layer or contact layer 1001 is formed on the bottom surface of substrate wafer over the insulating layer 701 and over the standoffs according to a pattern. One portion, relative to each finished device, of contact layer 1001 connects with the exposed portion of electrical connection points 101. The standoffs are then removed, leaving behind compliant conductive member 1001 and gap 1002. For one embodiment, coating layer 1101 is deposited on the bottom of the of substrate wafer.

Figure 14:
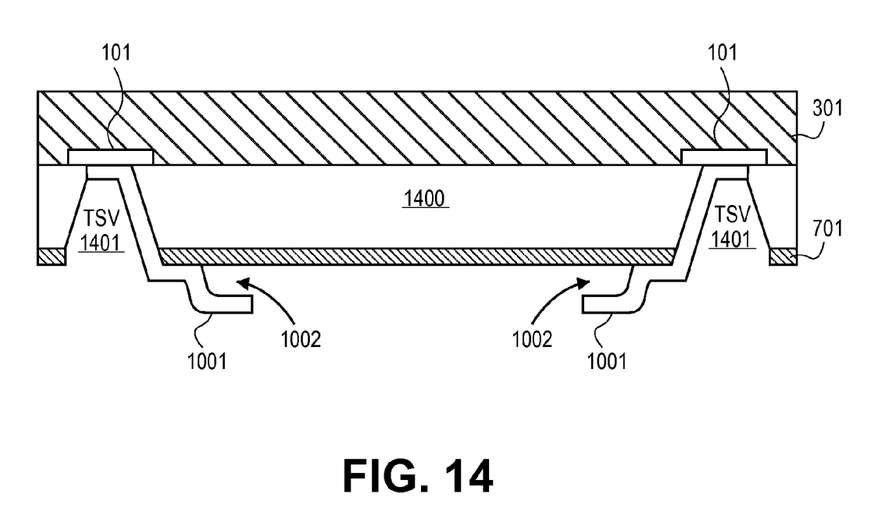
FIG. 14 is a cross-sectional side view according to an alternative embodiment in which the flexible contacts are coupled to the electrical connection points by way of through-silicon vias.

FIG. 14 is a cross-sectional side view according to an alternative embodiment in which the flexible conductive contacts 1001 are coupled to the electrical connection points by way of through-silicon vias (TSV) 1401. The fabrication of that embodiment is done in a manner similar to the process described above in reference to FIGS. 3-13. Vias 1401 are formed by etching, for example. Conductive layer 1001 is formed in a manner similar to that of layer 901 of FIG. 9—i.e., layer 1001 can be formed by pattern plating, for example, over a standoff (not shown) that is later removed by photo imaging, chemical etching, plasma etching, or other known techniques.

In the foregoing specification, the invention has been described with reference to specific exemplary embodiments thereof. It will be evident that various modifications may be made thereto without departing from the broader spirit and scope of the invention. The specification and drawings are, accordingly, to be regarded in an illustrative sense rather than a restrictive sense.

What is claimed is:

1. An electronic component package comprising: a flexible conductor on a bottom side of a substrate, the substrate having an electronic circuit, wherein a gap of air defines the space between a portion of the flexible conductor and a portion of the bottom side of the substrate;
   an electrical connection point on the top side of the substrate; a dicing trench formed between the bottom side of the semiconductor and the top side of the semiconductor; and an electrical conductor connecting the flexible conductor on the bottom side of substrate with the electrical connection weight on the top side of the substrate through the dicing trench.

2. The electronic component package of claim 1, wherein the electrical connection point comprises one of the following: gold, silver, nickel, titanium, aluminum, tungsten, copper, platinum, or a combination thereof.

3. The electronic component package of claim 1, further comprising:
   an insulating layer between a portion of the bottom surface of the substrate and the flexible conductor.

4. The electronic component package of claim 1, further comprising:
   an encapsulant layer above the top surface of the substrate.

5. The electronic component package of claim 1, wherein the flexible conductor comprises one of the following: gold, silver, nickel, titanium, aluminum, tungsten, copper, platinum, or a combination thereof.

6. The electronic component package of claim 1, wherein the flexible conductor comprises a bottom layer to accept solder and a top layer to reject solder.

7. The electronic component package of claim 1, further comprising:
   a barrier metal layer on the top side of the flexible conductor, the top side of the flexible conductor being the side closest to the substrate.

8. An electronic component package comprising:
   a flexible conductor on a bottom side of a substrate, the substrate having an electronic circuit, wherein a gap of air defines the space between a. portion of the flexible conductor and a portion of the bottom side of the substrate;
   an electrical connection point on the top side of the substrate;
   wherein the flexible conductor is electronically coupled with an electrical connection point on the top side of the substrate by means of a through-silicon via formed in the bottom side of the substrate and the flexible conductor partially resides within the through-silicon via.

* * * * *